United States Patent
Baban et al.

(10) Patent No.: US 8,652,550 B2
(45) Date of Patent: Feb. 18, 2014

(54) HEALTH BEVERAGES COMPRISING CINNAMON EXTRACT AND METHODS OF MAKING AND USING THE SAME

(75) Inventors: Babak Baban, Augusta, GA (US); Mark Anthony Fields, Augusta, GA (US)

(73) Assignee: Hydro One, LLC, Greenwood, SC (US)

( * ) Notice: Subject to any disclaimer, the term of this patent is extended or adjusted under 35 U.S.C. 154(b) by 402 days.

(21) Appl. No.: 12/812,984

(22) PCT Filed: Jan. 15, 2009

(86) PCT No.: PCT/US2009/031095
§ 371 (c)(1), (2), (4) Date: Apr. 18, 2011

(87) PCT Pub. No.: WO2009/091885
PCT Pub. Date: Jul. 23, 2009

(65) Prior Publication Data
US 2011/0189336 A1    Aug. 4, 2011

Related U.S. Application Data

(60) Provisional application No. 61/021,435, filed on Jan. 16, 2008.

(51) Int. Cl.
A23L 1/304 (2006.01)

(52) U.S. Cl.
USPC ............. 426/74; 426/72; 426/73; 426/521; 426/648

(58) Field of Classification Search
USPC ............ 426/590, 549, 72, 73, 74, 638, 521
See application file for complete search history.

(56) References Cited

U.S. PATENT DOCUMENTS

| | | | |
|---|---|---|---|
| 6,200,569 B1 | 3/2001 | Cheng | |
| 6,339,952 B1 | 1/2002 | Potter et al. | |
| 7,000,793 B2 | 2/2006 | Roubal et al. | |
| 2002/0146463 A1 | 10/2002 | Clayton | |
| 2003/0068391 A1 | 4/2003 | Harris et al. | |
| 2004/0001817 A1 | 1/2004 | Giampapa | |
| 2004/0058034 A1 | 3/2004 | Mechansho et al. | |
| 2005/0256031 A1 | 11/2005 | Hageman et al. | |
| 2006/0013903 A1 | 1/2006 | Romero et al. | |
| 2006/0127505 A1* | 6/2006 | Haines et al. | 424/729 |
| 2006/0233828 A1 | 10/2006 | Romero | |
| 2007/0237845 A1* | 10/2007 | Lin et al. | 424/739 |
| 2008/0008781 A1* | 1/2008 | Sweeney | 426/61 |
| 2011/0064833 A1* | 3/2011 | Patell et al. | 424/739 |

FOREIGN PATENT DOCUMENTS

| | | |
|---|---|---|
| JP | 63296664 | 2/1988 |
| WO | WO 2006/110491 A2 | 10/2006 |
| WO | WO 2006/110491 A3 | 10/2006 |
| WO | 2007/098240 A2 | 8/2007 |
| WO | WO 2007/098240 A3 | 8/2007 |
| WO | 2009/057126 * | 7/2009 |

OTHER PUBLICATIONS

International Search Report and Combination Written Opinion, mailed Apr. 24, 2009 in re International Patent Application No. PCT/US2009/031095.
Sam's Club—Sweet Success, "GlucaSafe", Mar. 31, 2009—HTTP/www.samsclub.com—XP-002521894.
GlobeNewswire, "Sweet Success", Mar. 31, 2009—HTTP/www.globenewswire.com—XP-002521893.

* cited by examiner

*Primary Examiner* — Helen F Heggestad
(74) *Attorney, Agent, or Firm* — Gardner, Groff, Greenwald & Villanueva, P.C.

(57) ABSTRACT

Described herein are beverages that provide a number of heath benefits associated with elevated or high blood sugar levels. For example, the beverages are useful in potentiating insulin activity, treating hyperglycemia, and maintaining blood sugar levels in a subject afflicted with diabetes. The beverages are composed of distilled water, cinnamon extract, and sweetener. Vitamins, minerals, and nutrients can be added to the beverage to provide additional health benefits.

21 Claims, No Drawings

HEALTH BEVERAGES COMPRISING CINNAMON EXTRACT AND METHODS OF MAKING AND USING THE SAME

CROSS REFERENCE TO RELATED APPLICATIONS

This application claims priority upon U.S. provisional application Ser. No. 61/021,435, filed Jan. 16, 2008. This application is hereby incorporated by reference in its entirety for all of its teachings.

BACKGROUND

Diabetes, long considered a disease of minor significance to world health, is now taking its place as one of the main threats to human health in the 21st century.

The past two decades have seen an explosive increase in the number of people diagnosed with diabetes worldwide. Pronounced changes in the human environment, in human behavior and lifestyle have accompanied globalization resulting in escalating rates of both obesity and diabetes.

Diabetes is a chronic disease and a serious, lifelong condition. People with diabetes are unable to use the glucose in their food for energy. The glucose accumulates in the bloodstream, where it can damage the heart, kidneys, eyes and nerves. Left untreated, diabetes can develop devastating complications. It is one of the leading causes of death and disability in the United States.

The number of people in the world with diabetes is expected to more than double by 2030, with India, China, and the U.S. topping the list of countries with the most cases. Researchers estimate that 366 million people, or 4.4% of the world's population, will be diabetic by 2030, which is up from 171 million, or 2.8% of the population, in 2000. The increase is attributed primarily to population changes, including growth in the number of people over 65. These projections do not assess the effect of rising obesity rates in developed countries, so they are almost certainly underestimates. In the U.S. alone, the Centers for Disease Control and Prevention has predicted 29 million diagnosed diabetics by 2050. However, the new study, which includes undiagnosed cases, projects a steeper rise to 30.3 million by 2030.

The fact that the epidemic is most acutely felt in the developing world has significant and substantial implications for the healthcare systems of those countries. Many countries are already being overwhelmed by the need to treat diabetes and its complications, and only those individuals who can afford to pay for expensive treatments will be able to expect reasonable care.

Despite pharmacological advances in diabetes treatment, nutrition therapy (NT) remains an essential component of diabetes management and self-management education. NT for diabetes includes the process and the system by which nutrition care is provided for diabetic individuals and the specific lifestyle recommendations for that care.

An important element of nutrition therapy is water. One of the many health care concerns with diabetic patients is to staying hydrated. Water is important for everybody, but especially for diabetes-patients, because decrease of the hydration-level could cause serious health problems for diabetics. With diabetes the body is no longer capable of processing sugar or glucose independently, from nutrition.

That is because there is not enough or too little insulin being made by the body itself, or the insulin cannot do its work properly. The insulin hormone is necessary for the transport of glucose from the blood to the body tissues. If the glucose is not accepted by the body, it will release the glucose through the urine, which increases the rate of dehydration. Therefore, it is very important for diabetes patients to remain hydrated.

Thus, it would be desirable to have a beverage that provides a source of hydration for those afflicted with diabetes as well as contain other components that assist in diabetes management. It would also be desirable that the beverage contains no carbohydrates, no sugar, and no caffeine currently present in most beverages.

Finally, it would be advantageous that the beverage have a satisfactory taste so that the subject is encouraged to consume the beverage on a routine basis, which is important in the management of diabetes.

SUMMARY

Described herein are beverages that provide a number of heath benefits associated with elevated or high blood sugar levels. For example, the beverages are useful in potentiating insulin activity, treating hyperglycemia, and maintaining blood sugar levels in a subject afflicted with diabetes. The beverages are composed of distilled water, cinnamon extract, and sweetener. Vitamins, minerals, and nutrients can be added to the beverage to provide additional health benefits.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a vegetable oil" includes mixtures of two or more such oils, and the like.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are beverages that provide a number of heath benefits. In one aspect, the beverages described herein are useful in controlling blood sugar levels. Sudden fluctuations in blood sugar can result in a number of different symptoms. For example, subjects afflicted with diabetes can experience coronary heart disease, nephropathy, neuropathy, and retinopathy. Other symptoms can include dizziness, discomfort, and dehydration. Subjects with diabetes can experience sudden fluctuations in blood sugar, which can result in dizziness, discomfort, and dehydration. Persistent fluctuations in blood sugar that occur in diabetic patients are enough to cause cell damage. In other words, repeated deviations from normal blood sugar levels can activate damaging cellular events and impair critical cellular defense processes.

In one aspect, the beverages described herein can maintain blood sugar levels in a subject. The term "maintain" is defined herein as preventing or reducing the likelihood of the occurrence of significant fluctuations in blood sugar in a subject. Significant fluctuations include changes in blood sugar levels that can produce a harmful or deleterious effect on the subject, examples of which were described above. Alternatively, the beverages described herein can maintain blood sugar levels within healthy, acceptable ranges.

In other aspects, the beverages described herein are useful in treating hyperglycemia. Hyperglycemia is associated with an increased risk for all of the common late complications of diabetes mellitus, which are the major causes of excess morbidity and mortality in diabetics. Hyperglycemia is exemplified by higher than normal concentrations of glucose in the blood. The beverages described herein help reduce levels of blood sugar in a subject (i.e., treat) afflicted with hyperglycemia. Techniques for monitoring the response of the subject with hyperglycemia as well as fluctuations in blood sugar levels are known in the art. For example, the measurement of serum glycosylated proteins, such as hemoglobin, is the most reliable method for assessing long-term glycemic control in people with diabetes (Bunn Diabetes 30:613-617 (1981); MacDonald Human Pathol. 10:279-291 (1979); Mayer et al Clin. Chim Acta. 127:147-184 (1983); Schleicher et al J. Clin. Chem. Clin. Biochem. 27:577-587 (1989); Takara et al Diabetes Care 16:1313-1314 (1993); Takara et al Diabetes Care 18:440-447 (1995)).

In another aspect, the beverages described herein potentiate insulin activity in a subject upon consumption. As described above, insulin works to lower the blood sugar level by stimulating the uptake of glucose by cells. The pancreas produces insulin which is released in response to increased blood glucose concentrations. The term "potentiate" is defined herein as the ability of the beverage to elicit an insulin response when the subject experiences high blood sugar levels (i.e., hyperglycemia). Techniques for measuring insulin activity upon consumption of the beverage are known in the art. For example, fat cell assays can be used herein. In an exemplary embodiment, fat cells may be prepared from rat epididymal fat pads. Samples or water control are incubated with $^{14}$C-glucose, albumin, dextrose and fat cells. Glucose uptake by cells is determined by the amount of $^{14}CO_2$ generated. Insulin potentiation is calculated by dividing the radioactive $CO_2$ released in the presence of sample by that released in response to water control. For example, an insulin potentiating activity (IPA) of 1 indicates that the sample tested had no measurable effect on insulin action and has no insulin potentiating activity whereas an IPA of >1 shows a measurable insulin potentiating activity in a fat cell assay.

The amount of beverage required to elicit the desired response (e.g., maintain blood sugar levels, treat hyperglycemia, potentiate insulin activity) can vary depending upon the subject and the severity of the condition. Routine consumption of the beverages can address the problems associated with high blood sugar. For example, consumption of two 20 oz bottles of a beverage described herein per day may provide short-term and long-term relief for patients with elevated blood sugar levels. Additionally, the beverages can provide a number of other health benefits. For example, the beverages can provide antioxidant support to help protect healthy cells from free radical damage. Not only does the beverage provide substantial antioxidant support but it also may help in the prevention of obesity, high blood pressure, heart disease, and neuropathy, which are serious health risks associated with diabetes.

The beverages include the following components: (1) distilled water, (2) an extract of cinnamon, and (3) a sweetener. Each component will be discussed in detail below as well as optional components that can be included in the beverage.

The beverages are predominantly composed of water. As discussed above, water is especially important for diabetics. Dehydration can lead to weight loss, excessive thirst, weakness, and high glucose levels in individuals with diabetes.

This rise in glucose acts as an osmotic diuretic increasing urine load on the kidney. The kidney's ability to reabsorb glucose and other water-soluble nutrients is compromised thus allowing substantial loss of important vitamins such as $B_1$, $B_6$, and $B_{12}$ and minerals such as $Mg^{2+}$, $Zn^{2+}$, $Cr^{2+}$. Thus, water is an important component of the dietary management of diabetes since dehydration can limit diabetic control.

The water used in the beverages described herein can be filtered or distilled water. The water contains minimal to no electrolytes. For example, the beverages described herein can contain minimal to no sodium. Additionally, as will be described in greater detail below, the water contains no preservatives. Additionally, the beverage contains minimal to no added sugars (independent of the sweetener), carbohydrates, and caffeine. Thus, the beverages described herein contain minimal calories. The amount of water (and ultimately beverage) consumed by the subject can vary. In certain aspects, the subject may consume from 10 to 20 oz per serving one or more times a day, where the majority of the beverage is distilled water. In one aspect, the subject can consume two 16.9 oz bottles of beverage per day.

The extract of cinnamon is primarily responsible for addressing the elevated blood sugar levels and problems associated with this. An extract of cinnamon is used in order to avoid any impurities that may be present in a cinnamon source, which may provide undesirable side-effects. The cinnamon extracts and methods for producing the same disclosed in U.S. Pat. No. 6,200,569, which are incorporated by reference, can be used herein. In summary, cinnamon bark is extracted with water or a dilute acid. Not wishing to be bound by theory, it is believed the extract contains a variety of different chalcones, which are a type of polyphenol or flavonoid. One class of polyphenols that can be extracted from cinnamon is the phytochemical Type A polyphenols (e.g., methyl hydroxy chalcone polymer or "MCHP"). The extract can be further purified using techniques known in the art such as, for example, chromatography, molecular exclusion chromatography, affinity chromatography, HPLC, and gel electrophoresis. In one aspect, the cinnamon extract is Cinnulin PF™ manufactured by Integrity Nutraceuticals International.

The amount of cinnamon extract present in the beverage is in a sufficient amount to elicit a desired response (e.g., maintain blood sugar levels, treat hyperglycemia, potentiate insulin activity). In one aspect, the amount of extract is from 50 mg to 150 mg per 17 oz of beverage. In another aspect, the amount of extract is from 60 mg to 140 mg per 17 oz of beverage, 70 mg to 130 mg per 17 oz of beverage, 80 mg to 120 mg per 17 oz of beverage, 90 mg to 110 mg per 17 oz of beverage, 95 mg to 105 mg per 17 oz of beverage, or about 100 mg per 17 oz of beverage.

The beverages described herein also possess one or more sweeteners. The selection of the sweetener is based upon two considerations. First, the sweetener should not increase blood sugar levels or minimally increase blood sugar levels upon ingestion. Second, the sweetener should provide a satisfactory taste so that the subject will be motivated to consume the beverage on a routine basis. Thus, the beverage contains no sugar and is essentially calorie-free.

In one aspect, the sweetener is a natural sweetener. Examples of sweeteners useful herein include, but are not limited to xylitol, erythritol, or any combination thereof. In the case of xylitol, it is metabolized independently of insulin and is slowly absorbed by the body. Therefore, when xylitol is consumed, the rise in blood glucose and insulin response associated with the ingestion of glucose is significantly reduced. Xylitol also has 40% less calories than sugar, which is consistent with the objective of weight control for treating diabetes. Xylitol does not cause a sharp increase in blood sugar levels or the associated serum insulin response, which is usually seen following consumption of other carbohydrates. Finally, xylitol can inhibit the growth of Strep mutans that are the bacterial component of tooth decay. Thus, the use of xylitol and other natural sweeteners in the beverages described herein may be appropriate for children as a substitute for fruit juices that contain high amounts of sugar. A source of erythritol useful herein includes a product sold under the tradename TRUVIA™ manufactured by Cargill that is derived from the leaves of stevia plants. Another source of erythritol is sold under the tradename Zsweet® manufactured by Zsweet Inc.

In certain aspects, the sweetener may be an artificial sweetener. For example, sucralose can be used. In the case of sucralose, the human body does not recognize it as an actual sugar or carbohydrate. It has been demonstrated that sucralose has no effect on short or long-term blood glucose control for individuals with normal blood glucose levels or individuals with type I or type II diabetes. Commercially-available artificial sweeteners include, but are not limited to, Splenda®, acesulfame-K, and NutraSweet® (aspartame). The amount of sweetener can vary depending upon the selection of the sweetener and the desired level of sweetness of the beverage. In one aspect, the sweetener is from 5 g to 20 g per 17 oz of beverage, 7 g to 18 g per 17 oz of beverage, 9 g to 15 g per 17 oz of beverage, 11 g to 13 g per 17 oz of beverage, or about 12 g per 17 oz of beverage. In one aspect, when the sweetener is a natural sweetener, the sweetener is combination of xylitol and erythritol, where the amount of each sweetener is from 5 to 95% by weight of the total weight of the sweetener. In one aspect, the amount of xylitol is from 30% to 50%, or about 40% by weight of the total weight of the sweetener, the amount of erythritol is from 50% to 70%, or about 60% by weight of the total weight of the sweetener.

The beverages described herein can contain a number of different nutrients, minerals, and vitamins that provide numerous health benefits. Mineral and vitamin supplementation can maintain blood glucose control and manage secondary complications associated with diabetes. In one aspect, the beverage includes a trivalent chromium ion and a divalent magnesium ion. An example of a useful chromium salt for producing chromium ions includes, but is not limited to, chromium picolinate. A deficiency in chromium can lead to glucose intolerance and insulin resistance. Chromium may improve insulin sensitivity and blood glucose control. Chromium in combination with other components such as biotin may also reduce cholesterol levels. Subjects afflicted with diabetes have lower levels of magnesium. A deficiency in magnesium can cause impaired insulin secretion and reduced tissue sensitivity to insulin. In one aspect, the magnesium salt is that produces magnesium ion includes, but is not limited to, magnesium gluconate. In one aspect, the amount of chromium ion is from 0.010 mg to 0.100 mg per 17 oz of beverage, 0.015 mg to 0.080 mg per 17 oz of beverage, 0.020 mg to 0.050 mg per 17 oz of beverage, 0.025 mg to 0.035 mg per 17 oz of beverage, or about 0.030 mg per 17 oz of beverage. In another aspect, the magnesium ion is from 10 mg to 100 mg per 17 oz of beverage, 20 mg to 80 mg per 17 oz of beverage, 40 mg to 70 mg per 17 oz of beverage, 55 mg to 65 mg per 17 oz of beverage, or about 60 mg per 17 oz of beverage.

In another aspect, the beverage includes folic acid. Folic acid is needed to keep homocysteine (an amino acid by-product) levels in blood from rising. Elevated homocysteine levels create a risk for heart disease and may also be linked to several other diseases such as diabetes. In one aspect, the amount of folic acid is from 0.010 mg to 0.100 mg per 17 oz of beverage, 0.015 mg to 0.080 mg per 17 oz of beverage, 0.020 mg to 0.060 mg per 17 oz of beverage, 0.040 mg to 0.060 mg per 17 oz of beverage, or about 0.050 mg per 17 oz of beverage.

A number of different vitamins can be included in the beverage. In one aspect, the beverage includes thiamin (vitamin $B_1$), pyridoxine (vitamin $B_6$), and cobalamin (vitamin $B_{12}$). Patients suffering from diabetes have lower levels of B vitamins. B vitamins can reduce homocysteine levels, which can lead to coronary artery disease. Additionally, administration of B vitamins can improve symptoms of diabetic neuropathy and vascular disease. In one aspect, the amount of thiamin is from 0.100 mg to 0.500 mg per 17 oz of beverage, 0.150 mg to 0.300 mg per 17 oz of beverage, 0.200 mg to 0.250 mg per 17 oz of beverage, or about 0.225 mg per 17 oz of beverage. In another aspect, pyridoxine is from 0.10 mg to 1.00 mg per 17 oz of beverage, 0.20 mg to 0.750 mg per 17 oz of beverage, 0.40 mg to 0.60 mg per 17 oz of beverage, or about 0.5 mg per 17 oz of beverage. In a further aspect, the amount of cobalamin is from 0.0001 mg to 0.010 mg per 17 oz of beverage, 0.001 mg to 0.005 mg per 17 oz of beverage, 0.001 mg to 0.003 mg per 17 oz of beverage, or about 0.002 mg per 17 oz of beverage.

In other aspects, the beverage further includes vitamin C. Diabetics are at greater risk for vitamin C deficiency because of altered insulin levels that promote the uptake of vitamin C into cells. In one aspect, vitamin C is from 5 mg to 50 mg per 17 oz of beverage, 10 mg to 20 mg per 17 oz of beverage, or about 15 mg per 17 oz of beverage.

In a further aspect, the beverage includes vitamin D. Vitamin D deficiency is prevalent in Type II diabetics. Low blood levels of Vitamin D can interfere with the proper function of insulin-producing cells. Low Vitamin D levels can also result in an increase in the risk of insulin resistance, even in otherwise healthy individuals.

In one aspect, vitamin D is from 5 IU to 100 IU per 17 oz of beverage, 10 IU to 80 IU per 17 oz of beverage, 20 IU to 60 IU per 17 oz of beverage, 30 IU to 50 IU per 17 oz of beverage, or about 40 IU per 17 oz of beverage.

In another aspect, the beverage includes vitamin E. Individuals with low levels of vitamin E are more likely to develop Type I or Type II diabetes. In one aspect, vitamin E is from 1 IU to 20 IU per 17 oz of beverage, 5 IU to 10 IU per 17 oz of beverage, or about 7.5 IU per 17 oz of beverage.

In a further aspect, the beverage includes biotin. Biotin can improve liver and pancreatic function as well as reduce pain from diabetic nerve damage. In one aspect, the amount of biotin is from 0.010 mg to 0.200 mg per 17 oz of beverage, 0.025 mg to 0.100 mg per 17 oz of beverage, 0.050 mg to 0.100 mg per 17 oz of beverage, or about 0.075 mg per 17 oz of beverage.

In one aspect, the wherein the beverage comprises water, folic acid, thiamin ($B_1$), pyridoxine ($B_6$), cobalamin ($B_{12}$), biotin, magnesium ion, chromium ion, vitamin C, vitamin D, vitamin E, xylitol, erythritol, and an extract of cinnamon. In another aspect, the beverage comprises water, folic acid, ascorbic acid, citric acid, thiamin ($B_1$), pyridoxine ($B_6$), cobalamin ($B_{12}$), biotin, magnesium gluconate, chromium picolinate, vitamin C, vitamin D, vitamin E, xylitol, erythritol, and an extract of cinnamon. In a further aspect, the beverage includes the following ingredients in water (distilled or purified):

| Component | Amount per Serving (16.9 oz) |
|---|---|
| Folic acid | .050 mg |
| Thiamin ($B_1$) | .225 mg |
| Pyridoxine ($B_6$) | .5 mg |
| Cobalamin ($B_{12}$) | .002 mg |
| Biotin | .075 mg |
| Magnesium | 60 mg |
| Chromium | .030 mg |
| Vitamin C | 15 mg |
| Vitamin E | 7.5 IU |
| Vitamin D | 40 IU |
| Cinnulin PF ® (Cinnamon extract) | 100 mg |
| Xylitol | 12 g |

In a further aspect, the beverage includes the following ingredients in water (distilled or purified):

| Component | Amount per Serving (16.9 oz) |
|---|---|
| Folic acid | .050 mg |
| Thiamin ($B_1$) | .225 mg |
| Pyridoxine ($B_6$) | .5 mg |
| Cobalamin ($B_{12}$) | .002 mg |
| Biotin | .075 mg |
| Magnesium | 60 mg |
| Chromium | .030 mg |
| Vitamin C | 15 mg |
| Vitamin E | 7.5 IU |
| Vitamin D | 40 IU |
| Cinnulin PF ® (Cinnamon extract) | 100 mg |
| Xylitol | 5 g |
| Truvia ® (erythritol) | 5 g |

Each of the formulations above can include additional ingredients such as, for example, ascorbic acid, citric acid, and natural flavorants.

The beverages described herein can be made and bottled using techniques known in the art for making beverages for human consumption. In one aspect, the beverage is prepared by a hot-fill process. The hot-fill process is the procedure by which containers are filled with a beverage at a high temperature and capped soon thereafter to ensure continued sterility of the container and product during and after the fill process. Thus, no preservatives are needed or added to the beverage. In one aspect, the different components of the beverage (e.g., cinnamon extract, sweetener, vitamins, minerals, etc.) are added to the distilled water under hot-fill conditions (e.g., 192° F.). The hot composition is then introduced into a suitable container composed of, for example, a polyolefin (e.g., polyethylene, polypropylene), a polyester (e.g., PET), or glass. The hot-fill techniques disclosed in U.S. Pat. Nos. 7,000,793 and 6,339,952, which are incorporated by reference for their teachings, can be used herein. After the beverages have been introduced into the bottles and capped, the beverages can be stored at room temperature for several months.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A beverage comprising (1) distilled water, (2), a water extract of cinnamon, (3) a sweetener comprising xylitol, (4) a trivalent chromium ion, (5) a divalent magnesium ion, (6) folic acid, (7) thiamin ($B_1$), (8) pyridoxine ($B_6$), (9) cobalamin ($B_{12}$), (10) biotin, (11) vitamin C, (12) vitamin D, and (13) vitamin E wherein the amount of extract of cinnamon is from 50 mg to 150 mg per 17 oz of beverage, and wherein the amount of trivalent chromium ion is from 0.010 mg to 0.100 mg per 17 oz of beverage.

2. The beverage of claim 1, wherein the amount of extract of cinnamon is from 95 mg to 105 mg per 17 oz of beverage.

3. The beverage of claim 1, wherein the sweetener comprises xylitol and erythritol.

4. The beverage of claim 1, wherein the sweetener is from 5 g to 20 g per 17 oz of beverage.

5. The beverage of claim 1, wherein the sweetener is from 11 g to 13 g per 17 oz of beverage.

6. The beverage of claim 1, wherein the sweetener is not an artificial sweetener.

7. The beverage of claim 1, wherein the beverage contains no added sugar and no caffeine.

8. The beverage of claim 1, wherein the beverage contains no preservatives.

9. The beverage of claim 1, wherein the beverage contains no sodium.

10. The beverage of claim 1, wherein the trivalent chromium ion is derived from chromium picolinate.

11. The beverage of claim 1, wherein the beverage comprises water, folic acid, ascorbic acid, citric acid, thiamin ($B_1$), pyridoxine ($B_6$), cobalamin ($B_{12}$), biotin, magnesium gluconate, chromium picolinate, vitamin C, vitamin D, vitamin E, xylitol, and a water extract of cinnamon.

12. The beverage of claim 1, wherein the beverage further comprises one or more natural flavorants.

13. A method for making the beverage of claim 1 comprising using a hot-fill process.

14. The beverage made by the process of claim 13.

15. A method for maintaining the blood sugar level of a subject comprising consuming the beverage of claim 1.

16. A method for potentiating insulin activity in a subject comprising consuming the beverage of claim 1.

17. A method for treating hyperglycemia in a subject comprising consuming the beverage of claim 1.

18. The method of claim 15, wherein the beverage maintains blood sugar levels in a subject with diabetes.

19. The method of claim 15, wherein the subject consumes two 20 oz bottles of the beverage per day.

20. The beverage of claim 1, wherein the divalent magnesium ion is derived from magnesium gluconate.

21. The beverage of claim 1, wherein the amount of the divalent magnesium ion is from 10 mg to 100 mg per 17 oz of beverage.

* * * * *